United States Patent
Matsuda et al.

(10) Patent No.: US 7,883,660 B2
(45) Date of Patent: Feb. 8, 2011

(54) STERILE PACKAGE, PROCESS FOR PRODUCING THE SAME, AND PRODUCTION APPARATUS

(75) Inventors: Naoto Matsuda, Yokohama (JP); Tsutomu Iwasaki, Yokohama (JP)

(73) Assignee: Toyo Seikan Kaisha, Ltd., Chiyoda-ku, Tokyo (JP)

( * ) Notice: Subject to any disclaimer, the term of this patent is extended or adjusted under 35 U.S.C. 154(b) by 286 days.

(21) Appl. No.: 11/815,751

(22) PCT Filed: Feb. 3, 2006

(86) PCT No.: PCT/JP2006/301872
§ 371 (c)(1),
(2), (4) Date: Nov. 18, 2008

(87) PCT Pub. No.: WO2006/085490
PCT Pub. Date: Aug. 17, 2006

(65) Prior Publication Data
US 2009/0200191 A1 Aug. 13, 2009

(30) Foreign Application Priority Data
Feb. 8, 2005 (JP) ............................. 2005-031296

(51) Int. Cl.
*B29C 39/02* (2006.01)

(52) U.S. Cl. ...................... 264/524; 264/525; 604/204; 604/212; 604/216

(58) Field of Classification Search ................. 206/438, 206/363, 364, 570–572; 264/524, 525, 534, 264/540, 571; 604/204, 212, 216, 28
See application file for complete search history.

(56) References Cited

U.S. PATENT DOCUMENTS

| | | | | |
|---|---|---|---|---|
| 2,667,165 A | * | 1/1954 | Smith | 604/204 |
| 4,018,222 A | * | 4/1977 | McAleer et al. | 604/113 |
| 4,548,601 A | * | 10/1985 | Lary | 604/204 |
| 4,707,966 A | | 11/1987 | Weiler | |
| 4,955,871 A | * | 9/1990 | Thomas | 604/217 |
| 5,687,550 A | | 11/1997 | Hansen | |
| 5,836,922 A | * | 11/1998 | Hansen et al. | 604/214 |

(Continued)

FOREIGN PATENT DOCUMENTS

JP 35-024295 9/1960

(Continued)

*Primary Examiner*—Luan K Bui
(74) *Attorney, Agent, or Firm*—Christensen O'Connor Johnson Kindness PLLC

(57) ABSTRACT

The present invention is directed to providing a sterile package (1, 1') integrally housing a contents-pouring device (5, 5') which has improved contents pourability and tamper evidence. According to the present invention, the sterile package (1, 1') can be efficiently produced by adopting the following steps of: (1) disposing a parison (27) in a mold (32) for a plastic container main body, (2) blowing sterile air from a nozzle (24) inserted in the parison (27) to blow-mold the plastic container main body, (3) filling the plastic container main body (2) with contents through the nozzle (24) and retracting the nozzle (24), (4) inserting a contents-pouring device (5, 5') in the parison located above the plastic container main body (2), (5) clamping a mold (31) for a protective case, and (6) forming a protective case (6) with the parison located above the container main body (2).

1 Claim, 7 Drawing Sheets

U.S. PATENT DOCUMENTS

| | | |
|---|---|---|
| 5,921,430 A | 7/1999 | Hansen |
| 7,192,549 B2 * | 3/2007 | Hansen ....................... 264/524 |
| 2005/0156360 A1 | 7/2005 | Hansen |

FOREIGN PATENT DOCUMENTS

| | | |
|---|---|---|
| JP | 61-002380 B2 | 1/1986 |
| JP | 2002-046725 A | 2/2002 |
| JP | 2002-078774 A | 3/2002 |
| JP | 2002-128126 A | 5/2002 |
| JP | 2003-026175 A | 1/2003 |
| JP | 2004-002271 A | 1/2004 |

* cited by examiner

US 7,883,660 B2

STERILE PACKAGE, PROCESS FOR PRODUCING THE SAME, AND PRODUCTION APPARATUS

This application is a 371 of PCT/JP2006/301872, filed Feb. 3, 2006.

1. Technical Field

The present invention relates to a sterile package which includes a contents--pouring device integrally housed therein, a method of producing the sterile package, and its production apparatus.

2. Background Art

Conventionally, a plastic container with a pouring device is known, in which the contents such as drugs and unregulated drugs are housed in a small volume to be used up at one time in the container, and a pouring device such as a needle for pouring the contents is attached to an inlet of the container (for example, see Patent Documents 1 and 2)

Further, it is also known that, when such a plastic container with a pouring device is produced, the container is filled with contents simultaneously at the time of molding the container in terms of sanitary supervision (see Patent Document 3)

Patent Document 1: Japanese Examined Utility Model Publication No. Sho 35-24295

Patent Document 2: Japanese Examined Patent Publication No. Sho 61-2380

Patent Document 3: JP 2002-128126 A

However, those containers with a pouring device have problems in that the container is opened due to an external force caused by a drop impact or the like in the course of production and distribution, and the container lacks a tamper-evident property for preventing mischief and unauthorized opening, and the like.

Therefore, in the plastic container with a pouring device filled with contents, an attempt is made so as to protect a pouring device and obtain a tamper-evident property by using a cladding such as a carton or a pouch, or by using another part such as a tape and a shrink-label. However, a method using a cladding and another part requires additional steps, which causes an increase in cost.

Then, in order to use up the contents housed in such a container at one time, it is necessary that the whole amount of contents be poured by crushing a container main body with fingers. However, in a case of a container in a cylindrical shape or the like, a bottom portion of the container becomes an obstacle, which makes it difficult to pour the contents completely.

Thus, in a conventional container with a pouring device, the pourability of contents is enhanced by adopting a container without a bottom portion, and thus, the container is not allowed to be self-supported.

DISCLOSURE OF THE INVENTION

Problem to be Solved by the Invention

Accordingly, the object of the present invention is to provide a sterile package which includes a pouring device integrally housed therein, in which the protection property of the pouring device, and the pourability of contents and tamper-evident property are enhanced. Another object of the present invention is to provide a method of producing the sterile package and its production apparatus, capable of continuously performing molding of a plastic container main body to be filled with contents, sterile filling of the contents, molding of a protective case that is formed integrally with the container main body, and storage of a pouring device in the protective case.

Means for Solving the Problem

In order to solve the above-mentioned problems, the present invention provides at least the following embodiments.

In one aspect, a sterile package is provided, comprising: a plastic container main body with a folding guide line formed to be filled with contents sterilely; a protective cast integrally molded with the plastic container main body; and a pouring device stored in the protective case.

In one embodiment, a sterile package is provided, in which the pouring device is stored in the protective case sterilely.

In another embodiment, a sterile package is provided, wherein the pouring device comprises a pouring part stored in a case sterilely and stored in the protective case.

In another embodiment, a sterile package is provided, further including a check part provided to a lower end of the pouring device.

In another aspect, a method is provided for producing a sterile package, including the following steps:

(1) disposing a parison in a mold for a plastic container main body;

(2) blowing sterile air from a nozzle inserted in the parison to blow-mold the plastic container main body;

(3) filling the plastic container main body with the contents from the nozzle and retracting the nozzle;

(4) inserting a pouring device in the parison located above the plastic container main body;

(5) clamping a mold for a protective case; and (6) forming the protective case with the parison located above the plastic container main body.

In one embodiment of the method, the nozzle is inserted or retracted while the sterile air is blown into the parison through the nozzle in such a manner that the nozzle does not come into contact with an inner wall of the parison. It is preferable that the pressure of the sterile air blown through the nozzle be set to be about 0.001 to 0.1 MPa.

In another embodiment, the method includes a pouring device insertion unit inserted or retracted while the sterile air is blown into the parison through an air hole provided to the pouring device insertion unit in such a manner that the pouring device insertion unit and the pouring device do not come into contact with an inner wall of the parison. It is preferable that the pressure of the sterile air blown through the air hole provided in the pouring device insertion unit be set to be about 0.001 to 0.1 MPa.

In another embodiment of the method, the parison between a lower portion of the pouring device and an upper portion of the plastic container main body is heat-sealed previously.

In another embodiment of the method, the protective case is formed by vacuum molding.

In another embodiment of the method, a blow pin is pierced in the protective case from a side surface of the protective case, and vacuum molding is performed while the sterile air is blown into the case from the blow pin. It is preferable that the pressure of the sterile air blown from the blow pin be set to be about 0.1 to 0.6 MPa.

In another embodiment of the method the parison is a multi-layered parison including a gas barrier resin layer.

In another aspect, a production apparatus for a sterile package is provided, the apparatus including a nozzle unit that supplies sterile air for blow molding and fills the contents of the container main body and a pouring device insertion unit in a sterile box, in which a parison extrusion die to be connected below the sterile box, a mold for a protective case, and a mold for a plastic container main body are successively disposed.

In one embodiment, the production apparatus comprises a mold for heat sealing provided between the mold for the protective case and the mold for the plastic container main body.

EFFECTS OF THE INVENTION

The present invention exhibits the following remarkable effects by employing the above-mentioned constituents.

(1) A sterile package of the present invention is excellent in a protection property of a pouring device and a tamper-evident property, and can prevent the opening of the package due to an external force in the course of production and distribution of the package, and the mischief and unauthorized opening of the package.

(2) In the sterile package of the present invention, a folding guide line is formed in a container main body, thereby contents can be easily poured completely.

(3) In the sterile package of the present invention, a backflow during pouring of the contents can be prevented by providing a check part to a lower end of the pouring device. Further, other contents such as a hazardous material (e.g., a stimulant) are prevented from being aspired after the use of the container and abusing of the package is prevented.

(4) According to a method of producing a sterile package of the present invention, molding of a plastic container main body to be filled with contents, sterile filling of the contents, molding of a protective case that is formed integrally with the container main body, and storage of a pouring device in the protective case can be performed continuously. Therefore, the sterile package can be produced efficiently at a low cost.

(5) A production apparatus of a sterile package of the present invention can be designed to be a compact size with a simple configuration, and the sterile state of the apparatus is managed easily, which can reduce a production cost significantly.

Figure 1:
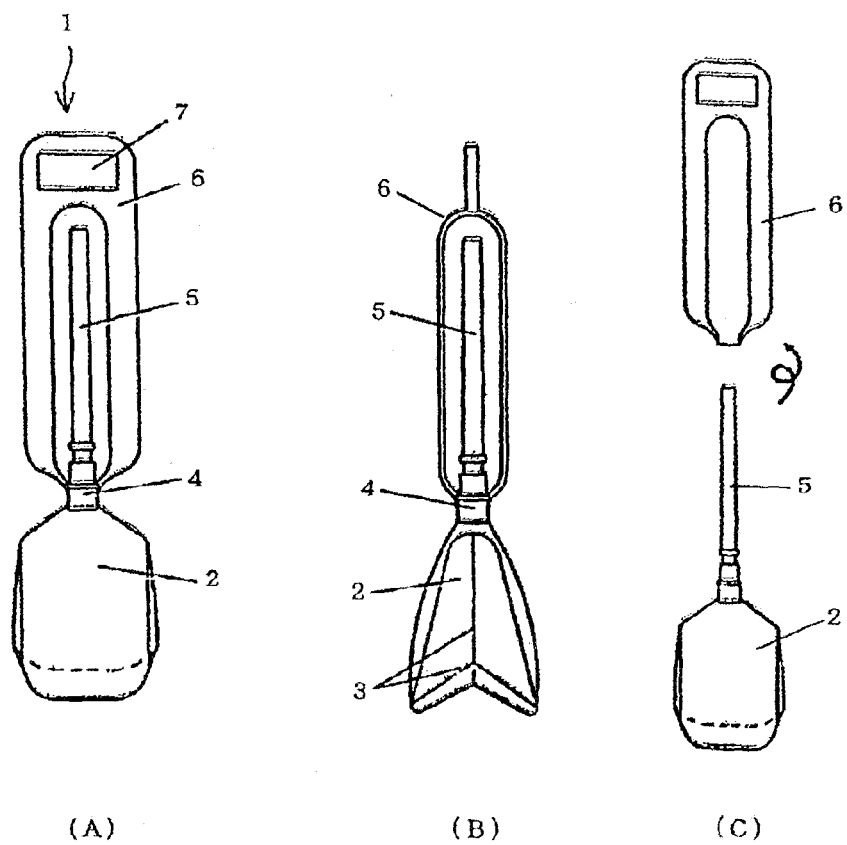
FIGS. 1A-1C represent views showing one example of a sterile package (disposable injection substance package) of the present invention.

DESCRIPTION OF REFERENCE NUMERALS 1,1' sterile package
2 plastic container main body
3 folding guide line
4,15 connecting portion
5 pouring device (needle unit)
5' pouring device (pouring part)
6 protective case
7 label
8 thin portion
9 tip end
11 case
12 stopper
13 hub
14 double-ended needle
16 stopper
17 check valve
21 sterile package production apparatus
22 sterile box
23 nozzle unit
24 nozzle
25 pouring device magazine
26 pouring device insertion unit
27 parison
28 die head
29 parison extruder
30 mold
31 mold for protective case
32 mold for container main body
33 mold for heat sealing
34 blow pin
M1,M2 driving device
P1 supply pipe of sterile air
P2 contents supply pipe

BEST MODE FOR CARRYING OUT THE INVENTION

Hereinafter, an example in which the present invention is applied to a disposable injection substance package will be described with reference to the drawings. It should be noted that the present invention is not limited to the following specific examples.

Figure 2:
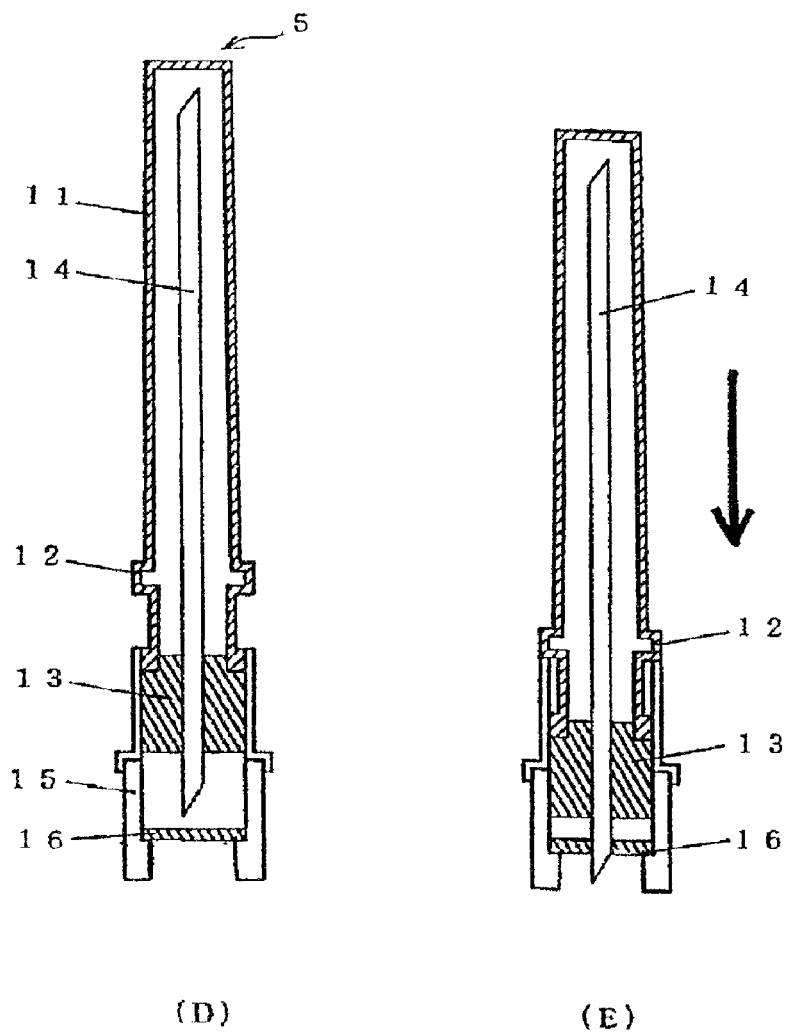
FIGS. 2D and 2E illustrate enlarged cross-sectional views showing a pouring device (needle unit) of the sterile package illustrated in FIGS. 1A-1C.

FIGS. 1 and 2 are views showing one example of a sterile package (disposable injection substance package) of the present invention. FIG. 1(A) is a front view of a package, FIG. 1(B) is a partial cross-sectional side view, and FIG. 1(C) is a view showing a state in which a protective case of a pouring device of the package is opened. Further, FIG. 2 are enlarged cross-sectional views of a pouring device (needle unit) of the package. FIG. 2(D) is a view showing a state of the pouring device (needle unit) before being used, and FIG. 2(E) is a view showing a state in which an injection substance needle of a pouring part constituting the pouring device is communicated with a container main body.

The injection substance package 1 is obtained by integrally molding a container body 2 provided with a folding guide line 3 and a protective case 6 storing a pouring device (needle unit) 5 composed of a double-ended needle 14 or the like of the pouring part for pouring contents and a case 11. The container body 2 is filled with an injection substance sterilely during molding of the container body 2. Further, a label 7 displaying the filled injection substance is provided on an upper portion of the protective case 6.

As shown in FIG. 2, in the pouring device 5, the double-ended needle 14 is fixed in the case 11 provided with a stopper 12 through a hub 13 composed of an elastic material of rubber or the like. At a lower end of a connecting portion 15 with respect to the container body 2 of the pouring device 5, a stopper 16 made of an elastic material of rubber or the like is set. In the pouring device 5, the double-ended needle 14 pouring contents is held in a sterile state in the case 11.

As shown in FIG. 1(C), when the injection substance package 1 is used, first, the protective case 6 is opened by twisting it with fingers. Next, when the case 11 of the pouring device 5 is pressed down to a position of FIG. 2(E), one end of the double-ended needle 14 of the pouring part fixed to the hub 13 passes through the stopper 16 to be communicated with the container body 2. Then, when the case 11 is removed and the other end of the double-ended needle 14 is inserted into the vein or the like of a patient, and the container body 2 is held with fingers, the container main body 2 is folded at the folding guide line 3, thereby the injection substance can be poured completely.

The injection substance package 1 can be self-supported under the condition that the double-sided needle 14 is communicated with the container main body 2. Thus, before used for a patient after the opening of the protective case 6 of the package, the package can be self-supported temporarily in a storage case or the like without being contaminated.

Figure 3:
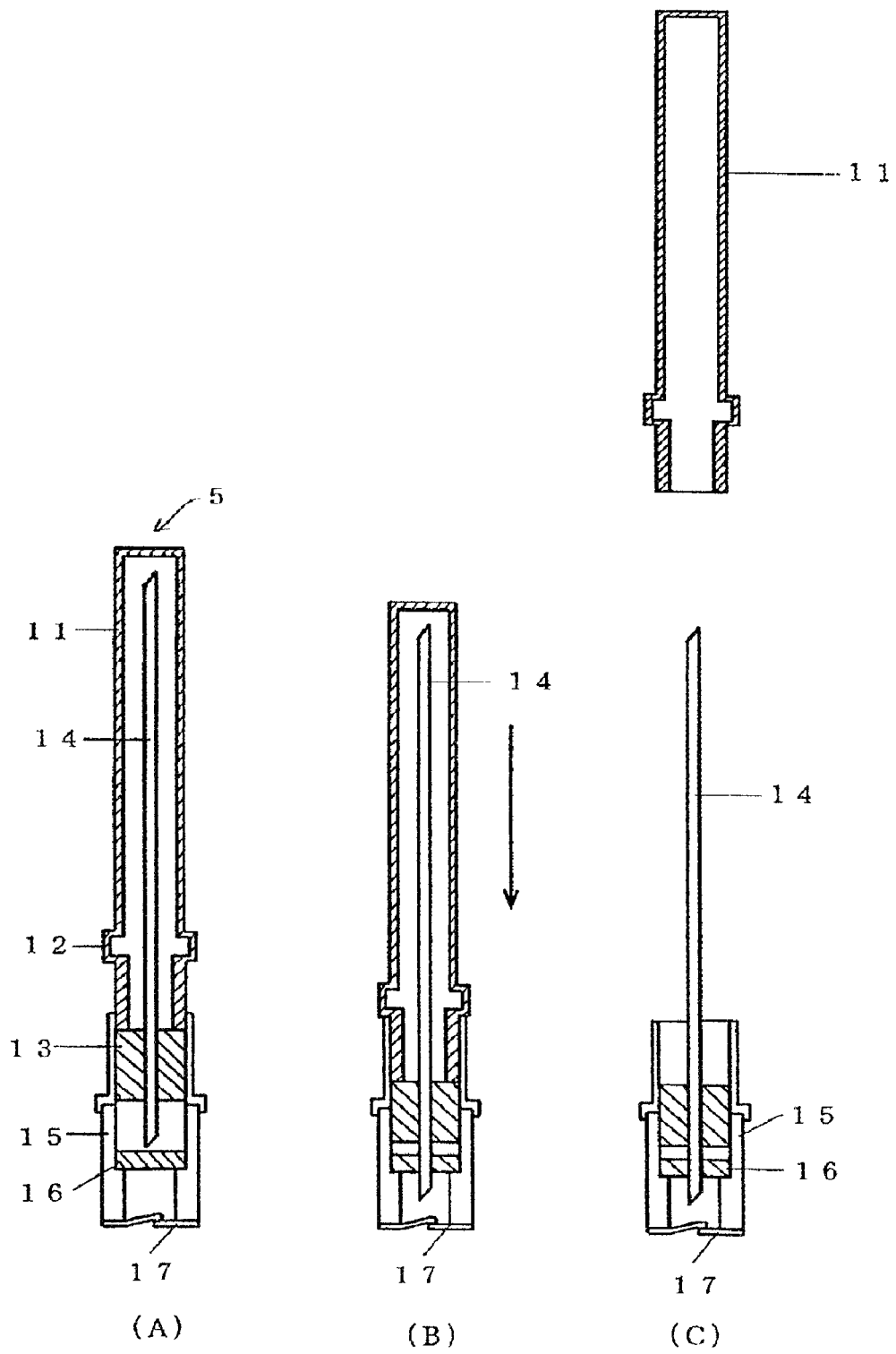
FIGS. 3A-3C illustrate enlarged cross-sectional views showing a pouring device (needle unit) of another example of the sterile package (disposable injection substance package) of the present invention.

FIG. 3 are enlarged cross-sectional views showing another example of the sterile package of the present invention, in which the pouring device (needle unit) 5 is shown in an enlarged state with the protective case 6 of the package being opened. FIG. 3(A) shows a state of the pouring device 5 before being used, and FIG. 3(B) shows a state in which the double-ended needle 14 of the pouring part is pushed in toward the container main body, thereby the double-ended needle 14 can be communicated with the container main body 2. Then, FIG. 3(C) shows a state in which the case 11 of the pouring device 5 is removed after the double-ended needle 14 is pushed in, thereby the injection substance in the container main body can be poured.

In the sterile package 1 of the present example, a check part such as a check valve 17 is provided to a lower end of the stopper 16 provided in the connecting portion 15 with respect to the plastic container main body 2 of the pouring device 5, that is, at the lower end of the pouring device 5.

By providing the check valve 17, the contents can be poured out of the container main body from the plastic container main body 2 via the double-ended needle 14, and the contents poured out or other drugs can he prevented from flowing back to the container main body 2 via the double-ended needle 14.

Then, by providing the check valve 17 to a lower end of the pouring device 5, other contents such as a hazardous material (e.g., stimulant) can be prevented from being aspired in the container after the use of the sterile package of the present invention and abusing of the container can be prevented.

Figure 4:
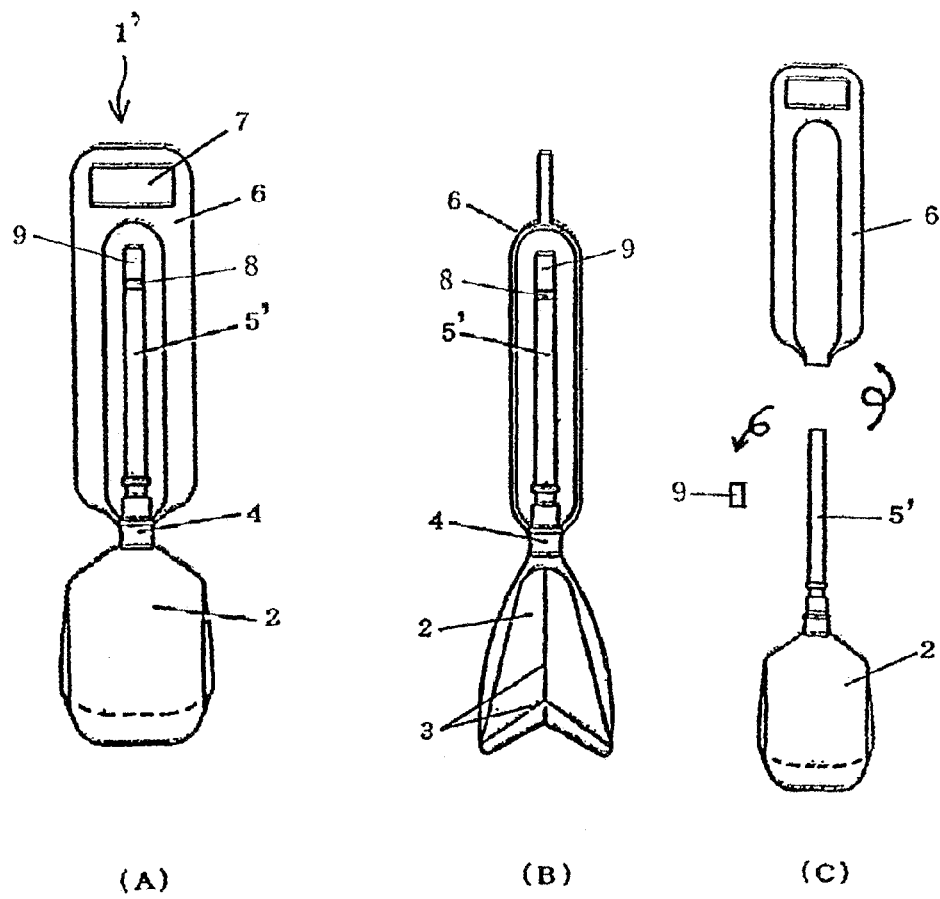
FIGS. 4A-4C illustrate views showing another example of the sterile package of the present invention.

FIG. 4 show another example of the sterile package of the present invention, and FIG. 4(A) is a front view of the package, FIG. 4(B) is a partial cross-sectional side view of the package, and FIG. 4(C) shows a state in which the protective case of the pouring device of the package is opened.

In this example, in the sterile package of FIG. 1, a pouring device 5' only composed of a cylindrical pouring part with a tip end blocked is used in place of the pouring device (needle unit) 5 composed of the double-ended needle 14 of the pouring part or the like and the case 11. The pouring device 5' is communicated with the container main body 2, without the case 11 in the needle unit 5, and a tip end 9 thereof is provided with an annular thin portion 8 for opening the tip end 9. When a package 1' is used, as shown in FIG. 4(C), the protective case 6 is opened by twisting it with fingers, and the thin portion 8 is folded to be removed to open the tip end 9. Then, when the pouring device 5' is applied to an affected portion of a patient, and the container main body 2 is held with fingers, the container main body 2 is folded at the folding guide line 3, thereby the contents can be poured completely. The sterile package 1' can be used preferably for storing, for example, a gel-shaped or cream-shaped suppository.

Figure 5:
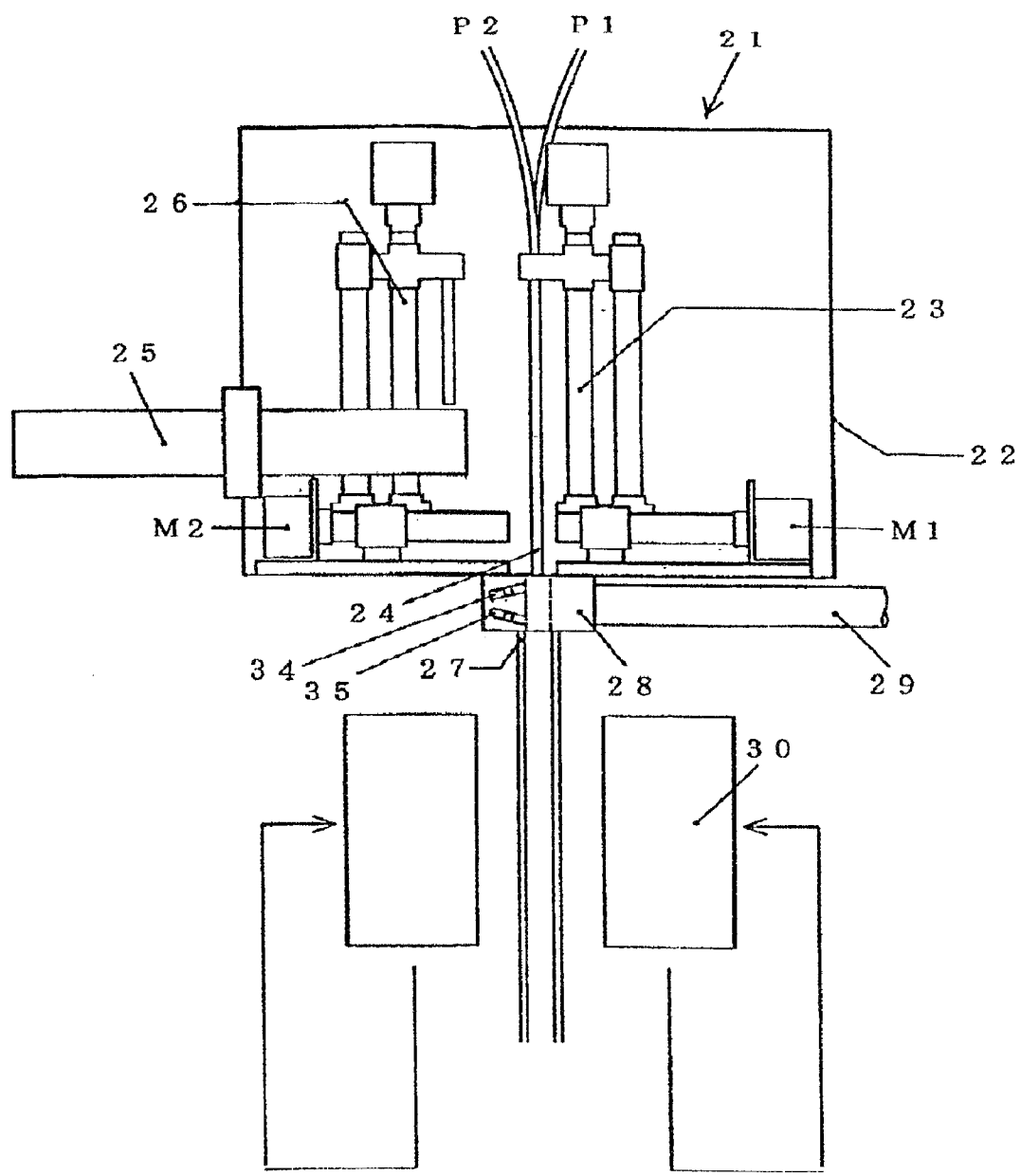
FIG. 5 is a schematic view showing one example of a production apparatus for the sterile package of FIGS. 1A-1C.
Figure 6:
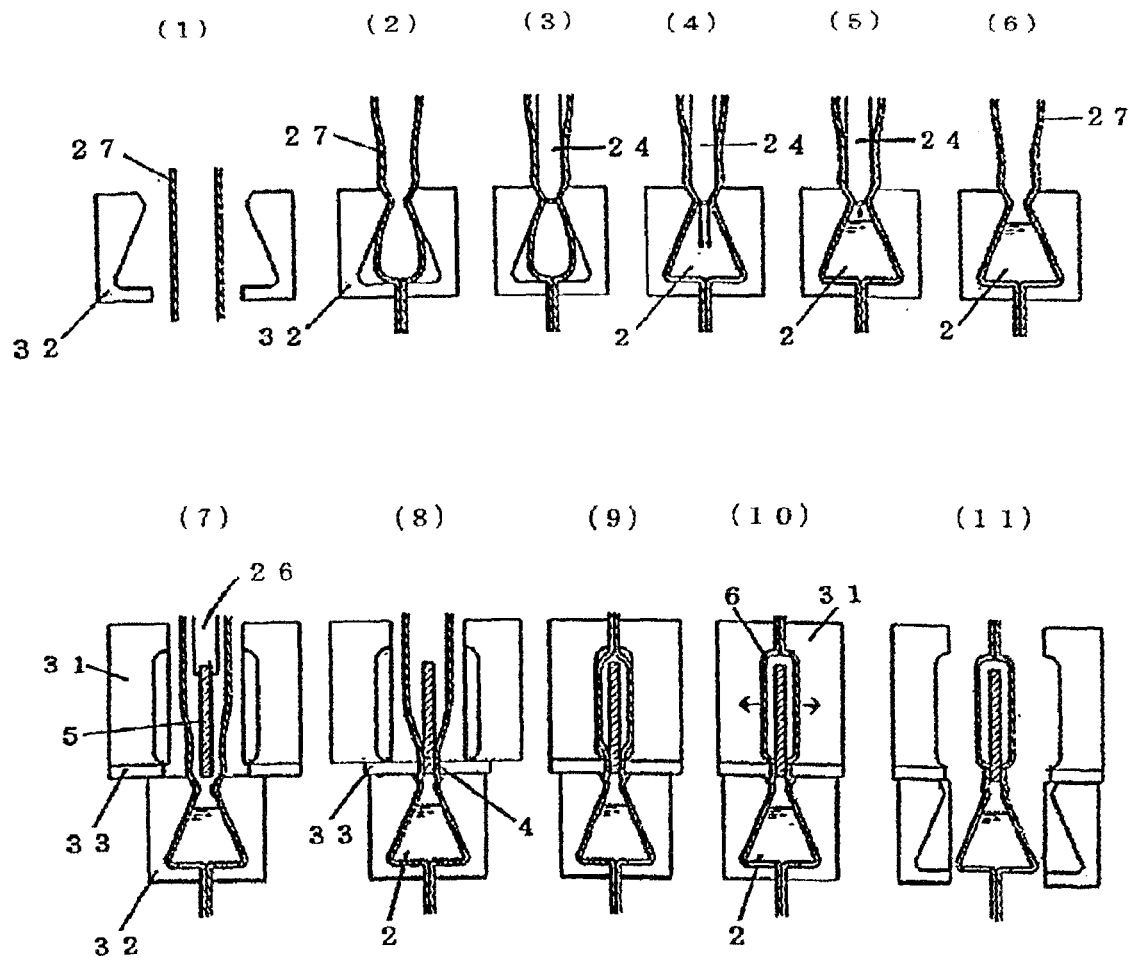
FIGS. 6(1)-6(11) are diagrams illustrating one example of a method of producing a sterile package using the production apparatus of FIG. 5.

Next, referring to the drawings, the production apparatus and production steps of the sterile package of the present invention will be described. FIG. 5 is a schematic view showing one example of the production apparatus of the sterile package of the present invention. FIG. 6 are schematic views illustrating one example of the steps of producing the sterile package of the present invention, using the production apparatus.

A production apparatus 21 stores, in a sterile box 22, a nozzle unit 23 having a nozzle 24 connected to a supply pipe P1 of sterile air for blow molding and a content supply pipe P2, and a pouring device insertion unit 26 having a pouring device magazine 25. The nozzle unit 23 and the pouring device insertion unit 26 can reciprocate alternately in a horizontal direction by driving devices M1 and M2, respectively.

A parison extruder 29 having a die head 28 extruding a parison 27 is set below the sterile box 22. On an inner side surface of the die head 28, there are provided an exit port 34 capable of discharging sterile air so that it becomes an ascending airstream from the die head side to the sterile box 22 so as to enhance sterility in the sterile box 22, and an exit port 35 capable of discharging sterile air so that it becomes a descending airstream so as to stabilize the shape of the parison by pressuring the inside of the parison. Further, a mold 30 for integrally molding the plastic container body and the protective case of the pouring device is provided below the parison extruder. The mold 30 is composed of a mold 31 for a protective case, a mold 32 for a plastic container main body, and a mold 33 for heat sealing for heat-sealing a connecting portion, which is disposed between the mold 31 for a protective case and the mold 32 for a container main body (see FIG. 6).

The sterile package of the present invention can be produced by the following steps (1) to (11), for example, using the production apparatus 21(see FIG. 6).

(1) The parison 27 is extruded to the mold 30.

(2) The mold 32 for a plastic container main body is clamped (first mold clamping).

(3) The nozzle 24 is inserted into the upper portion of the parison 27.

(4) The container main body is blow-molded with sterile air.

(5) The injection substance (contents) is filled in the container main body 2 from the nozzle 24.

(6) After the nozzle 24 is retracted from the upper portion of the parison 27, the position of a nozzle unit 23 in the sterile box 22 is exchanged with the position of a pouring device insertion unit 26.

(7) The pouring device 5 is inserted into the upper portion of the parison 27 by the pouring device insertion unit 26.

(8) The mold 33 for heat sealing is clamped, and the connecting portion 4 of the container main body 2 and the protective case 6 is heat-sealed.

(9) The mold 31 for a protective case is clamped, and the upper portion of the protective case 6 is heat-sealed, thereby the pouring device 5 is sealed in the protective case 6.

(10) The protective case 6 is molded by vacuum molding in the mold 31 for a protective case.

(11) All the molds are opened, and the parisons in the lower portion of the container body 2 and the upper portion of the protective case 6 are cut to obtain an intended sterile package.

Accordingly, the sterility of the contents of the container main body 2 and the inside of the protective case 6 is kept, and in a case where the pouring device (needle unit) 5 storing the double-ended needle 14 that is a pouring part of contents in the case 11 as shown in FIGS. 2 and 3 is used, or in a case where a pouring device 5' only composed of a cylindrical pouring part with a tip end blocked as shown in FIG. 4 is used, there is no fear that the pouring part may be contaminated before being used.

Figure 7:
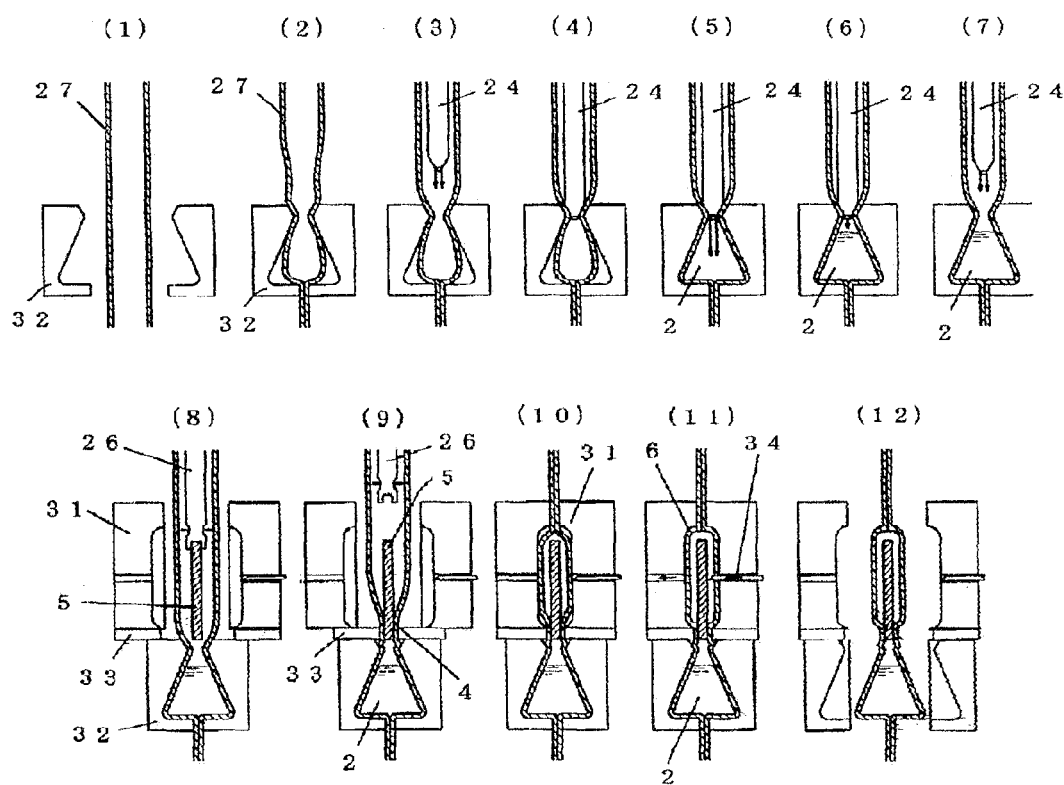
FIGS. 7(1)-7(12) are diagrams illustrating another example of the method of producing a sterile package of the present invention.

FIG. 7 are schematic views illustrating another example of the steps of producing the sterile package of the present invention.

(1) The parison 27 is extruded to the mold 30.

(2) The mold 32 for a plastic container main body is clamped (first mold clamping).

(3), (4) The nozzle 24 is inserted into the upper portion of the parison 27, while sterile air (Parison Control Air: hereinafter, referred to as "PCA") at a low pressure (about 0.001 to 0.1 MPa) is blown from a nozzle tip end portion to prevent the nozzle 24 from coming into contact with the inner wall of the parison.

(5) The container main body is blow-molded with sterile air.

(6) The injection substance (contents) is filled in the container main body 2 from the nozzle 24.

(7) While the PCA is blown into the parison 27, after the nozzle 24 is retracted from the upper portion of the parison 27, the position of a nozzle unit 23 in the sterile box 22 is exchanged with the position of a pouring device insertion unit 26.

(8) While the PCA at a low pressure (about 0.001 to 0.1 MPa) is blown into the parison 27 through air holes provided on the side wall of the pouring device insertion unit 26, the pouring device 5 is inserted into the upper portion of the parison 27 by the pouring device insertion unit 26.

(9) While the PCA is blown into the parison 27, the pouring device insertion unit 26 is retracted to clamp the mold 33 for heat sealing, thereby the connecting portion 4 of the container main body 2 and the protective portion 6 is heat-sealed.

(10) The mold 31 for a protective case is clamped, and the upper portion of the protective case 6 is heat-sealed, thereby the pouring device 5 is sealed in the protective case 6.

(11) A blow pin 34 is pierced into the protective case 6 from the side surface of the protective case 6, and while sterile air (about 0.1 to 0.6 MPa) is blown from the blow pin 34 to the protective case 6, the protective case 6 is molded by vacuum molding in the mold 31 for a protective case.

(12) All the molds are opened, and the parisons in the lower portion of the container body 2 and the upper portion of the protective case 6 are cut to obtain an intended sterile package.

The above-mentioned production steps (1) to (12) corresponding to FIG. 7 are obtained by modifying -the production steps (1) to (11) corresponding to FIG. 6.

In the first mold clamping step (2) and in the steps (3), (7), (8), and (9) of the insertion and retraction of the nozzle and the pouring device insertion unit, the cross-sectional shape of a parison may be deformed due to a change in an internal pressure or the like caused by the drawdown of the parison or the taking in/out of the nozzle and the pouring device insertion unit. Consequently, there arise a problem that the nozzle and the pouring device insertion unit or the pouring device come into contact with the parison inner wall, which makes it difficult to mold a sterile package. In the production steps of FIG. 7, the nozzle and the pouring device insertion unit are inserted/retracted while the PCA is blown, thereby a sterile package can be produced with good efficiency while avoiding such a problem.

The introduction of the PCA in the production steps of FIG. 7 may be performed continuously between the above-mentioned steps (3) and (9). In this case, it is not necessary to switch the introduction and suspension of the PCA for each step, and a sterile package can be produced with good efficiency while avoiding the above-mentioned problem.

Further, in a case of molding the protective case 6 only by vacuum molding, the protective case 6 is reduced in a pressure during molding. Therefore, a resistance preventing the molding of the case is generated, which makes it difficult to mold the protective case having a precise shape.

In the above-mentioned step (11), the blow pin 34 is pierced into the protective case 6 from the side surface of the protective case 6, and sterile air (about 0.1 to 0.6 MPa) is blown from the blow pin 34 to the protective case 6, thereby the inside of the protective case 6 is set in a positive pressure. Thus, when the vacuum molding of the protective case 6 is performed, the protective case 6 having a precise shape can be molded without a resistance caused by a reduced pressure. A label (not shown) or the like is attached to a hole remaining after the blow pin 34 is pulled out. At this time, the sterility in the protective case 6 may be impaired. However, in the sterile packages of FIGS. 2 and 3, by using the pouring device (needle unit) 5 storing the double-ended needle 14 that is a contents-pouring device in the case 11 in a sterile state, there is no fear that the pouring device 5 may be contaminated.

In the conventional technique, a production apparatus of a horizontal rotary system in which a number of molds are arranged successively so as to rotate or a shuttle system in which two molds reciprocate is used, the parison is extruded into the mold and the mold is clamped (corresponding to the step (2) of FIG. 6 or FIG. 7), the parison is cut, and the mold is moved, thereby the blow molding of the container main body and the filling of the contents are performed. It is practically impossible to dispose all the steps of such a production apparatus under a sterile environment, and thus, during cutting of the parison or the movement of the mold, the inside of the parison disposed in the mold may be contaminated with an outside air.

According to the present invention, a sterile package is produced without cutting a parison, using a production apparatus of a compact size with a simple configuration. This can greatly reduce the production cost with a simple management of the sterile state of the apparatus.

Further, in the sterile package of the present invention, the container main body 2 and the protective case 6 of the pouring device 5 are formed integrally. Therefore, the opening of the package caused by an external force during production or distribution, and the mischief and unauthorized opening of a package can be prevented.

In the present invention, there is no particular limitation on a material constituting the plastic container main body 2 and the protective case 6 formed integrally therewith, and any of the thermoplastic resin used for constituting a plastic container can be generally used. Examples of such a material include polyolefins such as low, middle, or high-density polyethylene, polypropylene, an ethylene-propylene copolymer, an ethylene-vinyl acetate copolymer (EVA), a saponified EVA, an ethylene-ethyl acrylate copolymer (EEA), an ion cross-linked olefin copolymer (ionomer); an aromatic vinyl copolymer such as polystyrene, a styrene-butadiene copolymer; a vinyl halide polymer such as polyvinyl chloride and vinylidene chloride resin; polyacrylic resin; a nitrite copolymer such as an acrylonitrile-styrene copolymer and an acrylonitrile-styrene-butadiene copolymer; polyamides such as nylon 6, nylon 66, and para or methaxylyleneadipamide; polyesters such as polyethylene terephtharate, polytrimethylene terephthalate, polybutylene terephtharate, and polyethylene naphtharate; various kinds of polycarbonates; fluorine resin; polyacetals such as polyoxymethylene; biodegrative reins such as polybutylene succinate, polyethylenesuccinate, polyhydroxybutyrate, polycaprolactone, and polylactic acid.

Examples of the preferable thermoplastic resin include polyolefin resin, in particular, polypropylene resin such as polypropylene, an ethylene-propylene copolymer.

The plastic container main body and the protective case of the present invention can have a single-layer configuration composed of one kind of resin layer or a multi-layered configuration composed of a plurality of resin layers.

In a case where the contents stored in the container main body require a gas barrier property as in medical drugs, it is preferable to produce a container with a multi-layered configuration including a gas barrier resin layer made of polyvinylidene chloride, a saponified EVA, polyamide resin, or a cyclic olefin copolymer, as an intermediate layer. Further, in a case where a much higher gas barrier property is required, a container with a multi-layered configuration including an oxygen absorbing resin layer containing an oxidizable polymer or the like can he used. Such a container with a multi-layered configuration can be produced using a multi-layered parison obtained using a die for multi-layer blowing by a conventional method in the steps shown in FIG. 6 or FIG. 7.

The invention claimed is:

1. A sterile package, comprising:
   a plastic container main body with a folding guide line formed therein to be filled with contents sterilely;
   a protective case integrally molded with the plastic container main body; and
   a needle unit sterilely stored in the protective case, the needle unit comprising:
      a double-ended needle stored sterilely in the protective case, the double-ended needle comprising a stopper end facing the main body of the container and an injection end facing away from the main body of the container;
      a stopper preventing liquid communication between the double-ended needle and the main body, wherein the stopper is configured to be punctured by the stopper end of the double-ended needle when the needle unit case is pressed toward the container main body, wherein puncturing the stopper with the stopper end of the double-ended needle provides liquid communication between the container main body and the injection end of the double-ended needle; and
   a check valve intermediate the stopper and the container main body, wherein the check valve is configured to allow liquid communication, when the stopper is punctured by the double-ended needle, from the container main body to the double-ended needle and to prevent liquid communication from the double-ended needle to the main body.

* * * * *